US012800479B2

(12) United States Patent
Piazza et al.

(10) Patent No.: US 12,800,479 B2
(45) Date of Patent: Nov. 17, 2026

(54) MEASUREMENT OF OPTICAL PROPERTIES OF A FLUID

(71) Applicant: Sensus Spectrum LLC, Morrisville, NC (US)

(72) Inventors: Vincenzo Piazza, Newmarket (GB); Michael Broom, Cambridge (GB); Hilary Meanwell, Saffron Walden (GB)

(73) Assignee: SENSUS SPECTRUM LLC, Morrisville, NC (US)

( * ) Notice: Subject to any disclaimer, the term of this patent is extended or adjusted under 35 U.S.C. 154(b) by 76 days.

(21) Appl. No.: 18/912,842

(22) Filed: Oct. 11, 2024

(65) Prior Publication Data

US 2025/0123198 A1 Apr. 17, 2025

(30) Foreign Application Priority Data

Oct. 12, 2023 (GB) ..................................... 2315663
Feb. 9, 2024 (GB) ..................................... 2401772

(51) Int. Cl.
*G01N 21/25* (2006.01)
*G01N 21/3577* (2014.01)
(Continued)

(52) U.S. Cl.
CPC ....... *G01N 21/255* (2013.01); *G01N 21/3577* (2013.01); *G01N 21/85* (2013.01); *G01N 33/18* (2013.01)

(58) Field of Classification Search
CPC ... G01N 2021/0314; G01N 2021/4769; G01N 21/251; G01N 21/255; G01N 21/3577;
(Continued)

(56) References Cited

U.S. PATENT DOCUMENTS

2015/0060674 A1 3/2015 Levels et al.
2023/0098744 A1* 3/2023 Seiwert ............. G01N 33/0039 436/135

FOREIGN PATENT DOCUMENTS

EP 2 846 161 A1 3/2015
EP 4 071 462 A1 10/2022
(Continued)

OTHER PUBLICATIONS

GB Intellectual Property Office, Combined Search and Examination Report for Application GB2401772.5, report dated Dec. 12, 2024, 10 pages.

(Continued)

*Primary Examiner* — Hina F Ayub
(74) *Attorney, Agent, or Firm* — Francis J. Maguire; WARE FRESSOLA MAGUIRE & BARBER LLP

(57) ABSTRACT

Apparatus for measuring at least one optical property, for instance turbidity, of a fluid, such as drinking water, is disclosed. The apparatus includes a measurement section having a conduit for the fluid, at least one light source, at least one photodetector, a diffuse reflecting surface, and a processing unit for processing at least one signal received from the at least one photodetector for use in determining the at least one optical property of the fluid. The at least one light source, the at least one photodetector and the diffuse reflecting surface are configured such that, when light is emitted by the at least one light source and the fluid is in the conduit, the light passes through the fluid and is reflected from the diffuse reflecting surface towards the at least one photodetector.

18 Claims, 6 Drawing Sheets

(51) Int. Cl.
*G01N 21/85* (2006.01)
*G01N 33/18* (2006.01)

(58) Field of Classification Search
CPC .................. G01N 21/53; G01N 21/85; G01N 2201/0636; G01N 2201/0637; G01N 33/18
See application file for complete search history.

(56) References Cited

FOREIGN PATENT DOCUMENTS

| | | | |
|---|---|---|---|
| JP | 2010-181150 | A | 8/2010 |
| WO | 2018/013035 | A1 | 1/2018 |

OTHER PUBLICATIONS

Machine translation into English of JP 2010-181150 A, 14 pages.

* cited by examiner

MEASUREMENT OF OPTICAL PROPERTIES OF A FLUID

BACKGROUND

The present invention relates to measurement of optical properties of a fluid, in particular, drinking water.

Drinking water is highly regulated, usually by a national regulator, such as, in the case of England and Wales, the Drinking Water Inspectorate. Standards and regulations specify requirements for water covering a range of parameters including micro-organisms, chemicals, metals and the way water looks and tastes including optical properties, such as turbidity and discoloration.

Turbidity and discoloration are properties that are most noticeable to end users and, thus, are most likely to be reported to the supplier (i.e., the utility company) by end users. It is desirable, therefore, for the utility company to be able to measure these optical properties, particularly at the point that it reaches the end user. This, however, may be impractical. Turbidity measuring instruments typically employ an arrangement in which a sample is illuminated with light at a specific wavelength from a given angle, and detecting the amount of light scattered at 90 degrees from the incident light direction. Such instruments are complex which places constraints on how and where they can be installed, which generally increases their cost, and ultimately places limits on the number of locations that turbidity can be monitored.

Reference is made to JP 2010 181150 A which describes measuring the concentration of a substance dissolved in a liquid. A light emitting body transmits light which passes through the solution to be measured, is reflected by a reflecting plate, passes through the solution again and is received by a light receiving body. The light emitting body and the light receiving body are arranged so that the optical axis of the light emitter is oriented at approximately 45 degrees with respect to the reflecting plate.

SUMMARY

According to a first aspect of the present invention there is provided apparatus for measuring at least one optical property of a fluid. The apparatus comprises a measurement section comprising a conduit for a fluid, at least one light source, at least one photodetector, a diffuse reflecting surface, and a processing unit for processing at least one signal received from the at least one photodetector for use in determining at least one optical property of a fluid. The at least one light source, the at least one photodetector and the diffuse reflecting surface are configured such that, when light is emitted by the at least one light source and the fluid is in the conduit, the light passes through the fluid and is reflected from the diffuse reflecting surface towards the at least one photodetector.

In the case of water, the apparatus can be provided in, or together with, a water meter, and so help sensors capable of measuring turbidity and discoloration to be deployed more widely throughout the water delivery network, particularly at points of use.

The light emitted by the at least one light source may pass along an optical axis which is normal to the diffuse reflecting surface or which is within 10 degrees from the normal to the diffuse reflecting surface. The light emitted by the at least one light source may pass radially across a cylindrical conduit. The light emitted by the at least one light source may pass along an optical axis which is parallel to the normal to the diffuse reflecting surface. The light emitted by the at least one light source may pass along an optical axis which is perpendicular to the axis of a cylindrical conduit. The light emitted by the at least one light source may pass along an optical axis which is perpendicular to a plane containing the axis of the cylindrical conduit.

The at least one light source and the at least one photodetector may be disposed on one side of measurement section.

The conduit may be a tube. The conduit may me be circular, elliptical or rectangular in cross section.

The at least one property may include color of the fluid and/or turbidity of the fluid.

The diffuse reflecting surface may be curved such as an annular section of a cylinder of material or an arced section of a cylinder of material. The diffuse reflecting surface may be or may be substantially white. The diffuse reflecting surface may comprise a coating on an inner surface of the conduit.

The at least one light source or each light source may be or may be substantially monochromatic and the at least one photodetector is broadband (expressed differently, able to detect more than one different wavelength) or vice versa.

The at least one light source and the at least one photodetector may be provided in a sensor unit comprising a housing.

At least one of the at least one light source and/or at least one of the at least one photodetector may be operable in the infrared band of the electromagnetic spectrum.

The processing unit may be configured to calculate a given parameter indicative of the quality of the fluid in dependence upon the at least one signal received from the at least one photodetector.

The fluid may be a liquid. The liquid may be water, such as, drinking water, for example, for human consumption. The fluid may be a gas.

The at least one light source may be activated for a duration and/or at a repetition rate depending on flow rate of fluid and/or an accumulated volume of fluid. For example, the apparatus may take a measurement every N liters, where N may be positive (corresponding to flow in a forward direction) or negative (corresponding to flow in a reverse direction, i.e., back flow), non-zero number, for example, greater than or equal to 10. This can be used to help reduce power consumption.

According to a second aspect of the present invention there is provided a fluid meter comprising a unit housing apparatus for measuring fluid flow through the meter and the apparatus of the first aspect.

According to a third aspect of the present invention there is provided a system comprising a fluid meter and the apparatus of the first aspect. The fluid meter and the apparatus are discrete units arranged such that fluid is communicated through the meter and then through the apparatus or vice versa.

According to a fourth aspect of the present invention there is provided computer system comprising at least one processor, memory and a network interface. The at least one processor is configured, in response to receiving a set of messages, such as measurements, alarms and/or codes, from a set of remote water meters at known locations relating to at least one water property, such as oxidation reduction potential, discoloration and/or turbidity, to detect a change in water being delivered to a given water meter and/or to a given sub-set of meters, and/or to determine a cause of a change in water being delivered to a given water meter and/or to a given sub-set of meters, and/or to determine a statistical estimate of a point of origin in a water network resulting in a change in water being delivered to a given water meter and/or to a given sub-set of meters, and/or to determine a severity of change in water being delivered to a given water meter and/or to a given sub-set of meters.

According to a fifth aspect of the present invention there is provided a drinking water delivery system comprising a set of remote water meters provided with or including a respective apparatus of the first aspect and deployed through a water supply network; and the computer system of the fourth aspect. The computer system is arranged to communicate with the set of remote water meters so as to receive the set of messages, such as measurements, alarms or codes.

According to a sixth aspect of the present invention there is provided a method of using the apparatus of the first aspect, the method comprising causing activation of the at least one light source or at least two light sources sequentially and processing signals, such as a sequence of signals, received from the at least one photodetector to determine at least one optical parameter.

The at least one light source may be active at a given repetition rate or given pattern and the least one photodetector may be read out in synchronization with activation of the at least one light source so as to increase read-out sensitivity.

According to a seventh aspect of the present invention there is provided an apparatus for measuring an optical parameter of a fluid comprising a measurement section that allows the measured fluid to flow through a round conduit, at least one light source, and at least one photodetector positioned substantially on one side of the measurement section, a curved diffuse reflecting surface positioned in a way to reflect outgoing light, that has passed through the measured fluid from the light source, back to the photodetector and an electronic processing unit.

The apparatus may comprise a water meter. The apparatus may be adjacent and/or connected to a fiscal grade water meter. The apparatus may be located inside the main body of a fiscal grade water meter.

The fluid may be drinking water.

The measured optical parameter may be discoloration and/or turbidity.

The diffuse reflector may be white in color. The diffuse reflector may comprise of a dye or coating applied to the measurement section.

The light source may be substantially monochromatic (either intrinsically or through filtering), and the photodetector is broadband or vice versa. Some or all the light sources and photodetectors may be contained in the same housing.

At least one light source or photodetector may be (are) substantially in the IR spectra.

The electronic processing unit may calculate water quality parameters, given the measurements taken by the photodetector(s).

According to an eighth aspect of the present invention there is provided a method using the apparatus of the first and/or seventh aspect, wherein multiple light sources, preferably of different spectral content, are illuminated sequentially, in such a way as to allow the photodetector to measure the response from each light source individually.

According to a ninth aspect of the present invention there is provided a drinking water delivery system comprising the apparatus of the first and/or seventh aspect, a collection of fiscal water meters installed in a water supply network wherein: at least some meters are capable of electronically communicating to a centralized storage and analysis unit; at least some meters have at least one additional sensor capable of measuring at least one property of the water; wherein the sensor is mounted within the water meter body and/or in line with the water meter in the main water stream, measuring at least one of the following ORP (oxidation reduction potential), discoloration, turbidity; and a centralized storage and analysis unit that uses stored data to detect changes in the water being delivered to a water meter and/or a group of meters and/or inferring the cause of the change and/or providing a statistical estimate of the origin point in the network and/or the severity of changes in the water being delivered.

The centralized storage and analysis unit may combine the flow data with the ORP and/or discoloration and/or turbidity data. The centralized storage and analysis unit may combine the water pressure data with the ORP and/or discoloration and/or turbidity data. The communication between the water meter and the centralized storage and analysis unit may use wireless communication protocols. The meter may have the capability of controlling the water quality sensor and request the measurement to be performed. The water quality sensor may measure independently at regular intervals and reports the information to the water meter. The centralized storage system can request at least one of the water meters to capture and can report an additional measurement based on the values already stored in the system based on the values stored in the centralized storage system.

BRIEF DESCRIPTION OF THE DRAWINGS

Certain embodiments of the present invention will now be described, by way of example, with reference to the accompanying drawings in which.

DETAILED DESCRIPTION OF CERTAIN EMBODIMENTS

Figure 1:
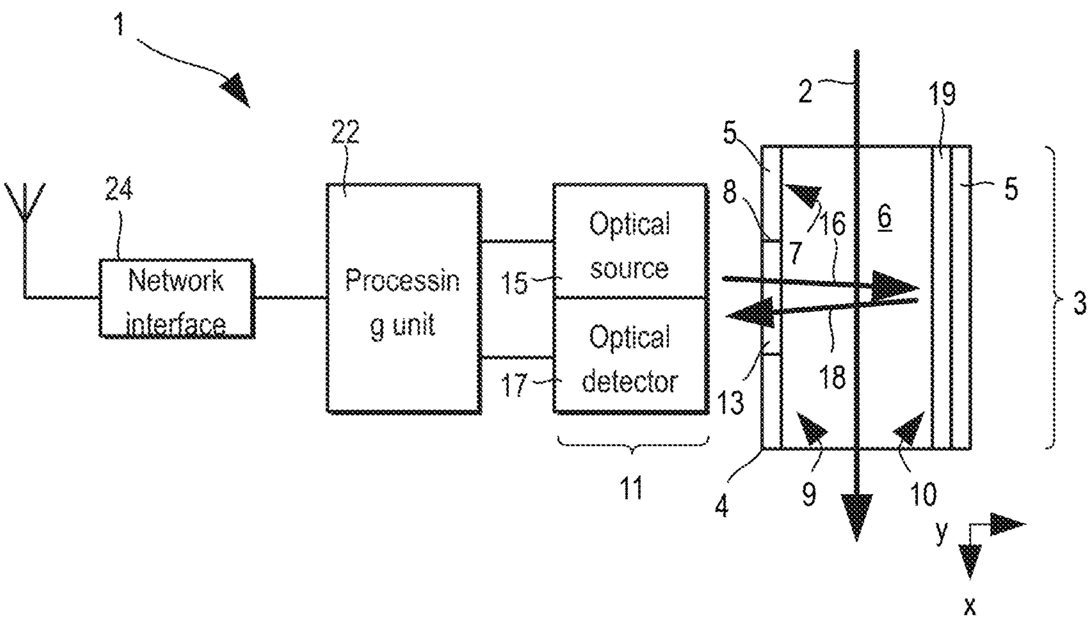
FIG. 1 is a schematic block diagram of apparatus for measuring optical properties of a fluid.

Turbidity is caused by the presence of suspended solids in water, usually caused by contamination with clay, silt, organic matter and micro-organisms, such as plankton. Turbidity is measured as the amount of light that is scattered when passing through water and is expressed in Nephelometric Turbidity Units (NTUs). Turbidity is visible from around 5 NTU. A high turbidity (typically considered to be greater than 5 NTUs) is an issue for water distribution utility companies because it can lead to customer complaints and also because it can be a contributing cause for an increase in bacterial contamination since bacteria find a suitable environment to replicate on the surface of the suspended particle.

An acceptable level of turbidity for water being introduced into the water network is typically less than 1 NTU, and an acceptable level at the tap is usually less than 4 NTUS.

Discoloration takes place when soluble compounds are released into the water, with the compound absorbing at specific wavelengths. A change in color is a direct indicator of the presence of dissolved molecules which can be caused by corrosion in the pipework or leaks in the pipe which lead to ingress of foreign material in the water stream. A change in color is one of the main causes for customer complaints even in cases where the dissolved compound is safe for human consumption.

Utility companies are interested in monitoring these parameters since they can help to detect issues in the network which are responsible for the majority of customer complaints and it can facilitate managed network operation. Because deposits tend to form during a period of constant flow, changing the flow conditions in the network (for example, by increasing flow in a specific section) can cause the deposits to be dissolved again. Without direct information, utility companies tend to change operating conditions very slowly to ensure water quality is not affected.

Apparatus is herein described which employs an optical sensor which can be mounted in-line in a water distribution system. The sensor can be installed in a dedicated port in a measurement section. The measurement section is connected to a water stream in an inline configuration so that all the water from the stream enters the inlet of the measurement section and is then returned from the outlet to the main stream. The sensor is able to measure the color of the water and can report it as an RGB triplet of values, plus a reference dark current measurement (that is, the signal detected by the photodiode without any LEDs illuminated). The values can then be used to obtain an intensity of the discoloration and the potential cause. Additionally, the sensor can also measure the turbidity level in the water using an infrared LED by detecting the light backscattered by the particles suspended in the water.

Turbidity can be used both as a standalone measurement and to correct the RGB values obtained via the discoloration measurement to compensate for the increased light levels detected on all three channels with increasing turbidity in the water.

Referring to FIG. 1, apparatus 1 (or a "sensor") for measuring at least one optical property of a fluid 2 is shown. In this case, the fluid 2 is water, in particular, drinking water and so the fluid 2 is hereinafter referred to as water.

Figure 2:
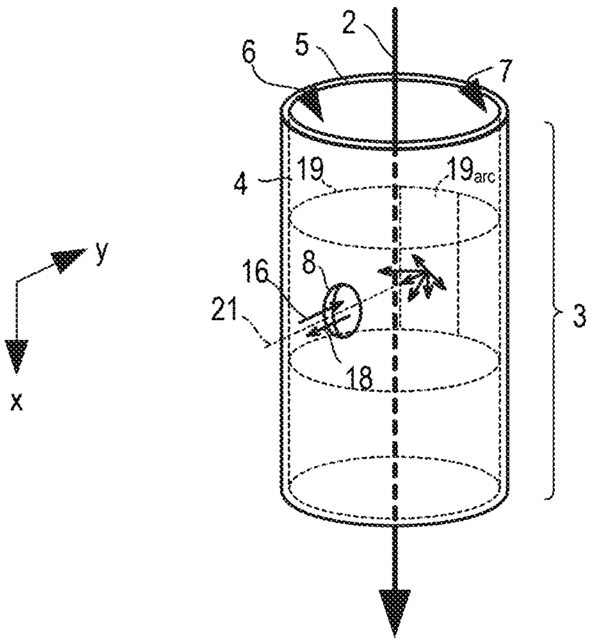
FIG. 2 is a schematic perspective view of a conduit.

Referring also to FIG. 2, water 2 flows, e.g., intermittently, through a measurement section 3 in the form of a section of pipe 4 (herein also referred to as a "conduit" or "flow tube"). The pipe 4 has a side wall 5, which defines a flow passage 6 (or "lumen"), and an inner surface 7. The pipe 4 includes an aperture 8 (or "port") in the side wall 5 on a first side 9 of the pipe 4. A typical size of the pipe 4 is between ½ inch (13 mm) and 1 inch (25 mm) inner diameter, although the pipe 4 may have a smaller or bigger inner diameter.

The apparatus 1 includes an optical sensor 11 which can take the form of a single unit having a housing 12 and an optical window 13 which can be arranged to form a watertight enclosure and/or an optically-clear potting compound 14, such as a polyurethane-based resin, filling the housing 12. The optical window 13 may be formed of a suitable material, such as glass, Plexiglass® or quartz. The window 13 may be flat or curved. The optical sensor 11 includes at least one light source 15 (or "optical source"), for example, in the form of one or more light-emitting diodes (LEDs), for emitting light 16, and at least one optical detector 17 (or "light detector"), for example, in the form of one or more photodiodes, for measuring intensity of received light 18. The apparatus 1 also includes a diffuse reflecting surface 19 (or "diffuse reflector") which is disposed on the inside of the pipe 4 on a second side 10 of the pipe 4. As will be explained in more detail hereinafter, the diffuse reflector 19 can be provided by the inner surface 7 of the pipe 4. The optical sensor 11 is disposed in or over the aperture 8 and may be secured using a suitable sealant (not shown), for instance, epoxy, and/or using a suitable retainer (not shown), such as a clip or band.

The at least one optical source 15 and the diffuse reflector 19 are positioned and orientated so as to direct light 16 through the aperture 8 along an optical axis 21 into the pipe 4, towards the diffuse reflector 19 so that it passes through the flow passage 6 and, thus, the water 2 when present in the pipe 4. The at least one optical detector 17 and the diffuse reflector 19 are positioned and orientated so that the diffuse reflector 19 reflects the light 16 back towards the at least one optical detector 17 substantially along the optical axis 21. The optical axis 21 is preferably normal to the diffuse reflector 19. Thus, the optical sensor 11 is arranged to be perpendicular to the longitudinal axis of the conduit 4.

A reflector may be considered to be a diffuse reflector if it reflects more than 90% of the incident light in a specific wavelength range, of which more than 50% is diffusely reflected according to Lambert's cosine law.

The apparatus 1 includes a processing unit 22 which is used to drive the at least one optical source 15 and to receive a signal from the at least one optical detector 17. The apparatus 1 may include a power source (not shown), for example in the form of a battery.

Figure 8:
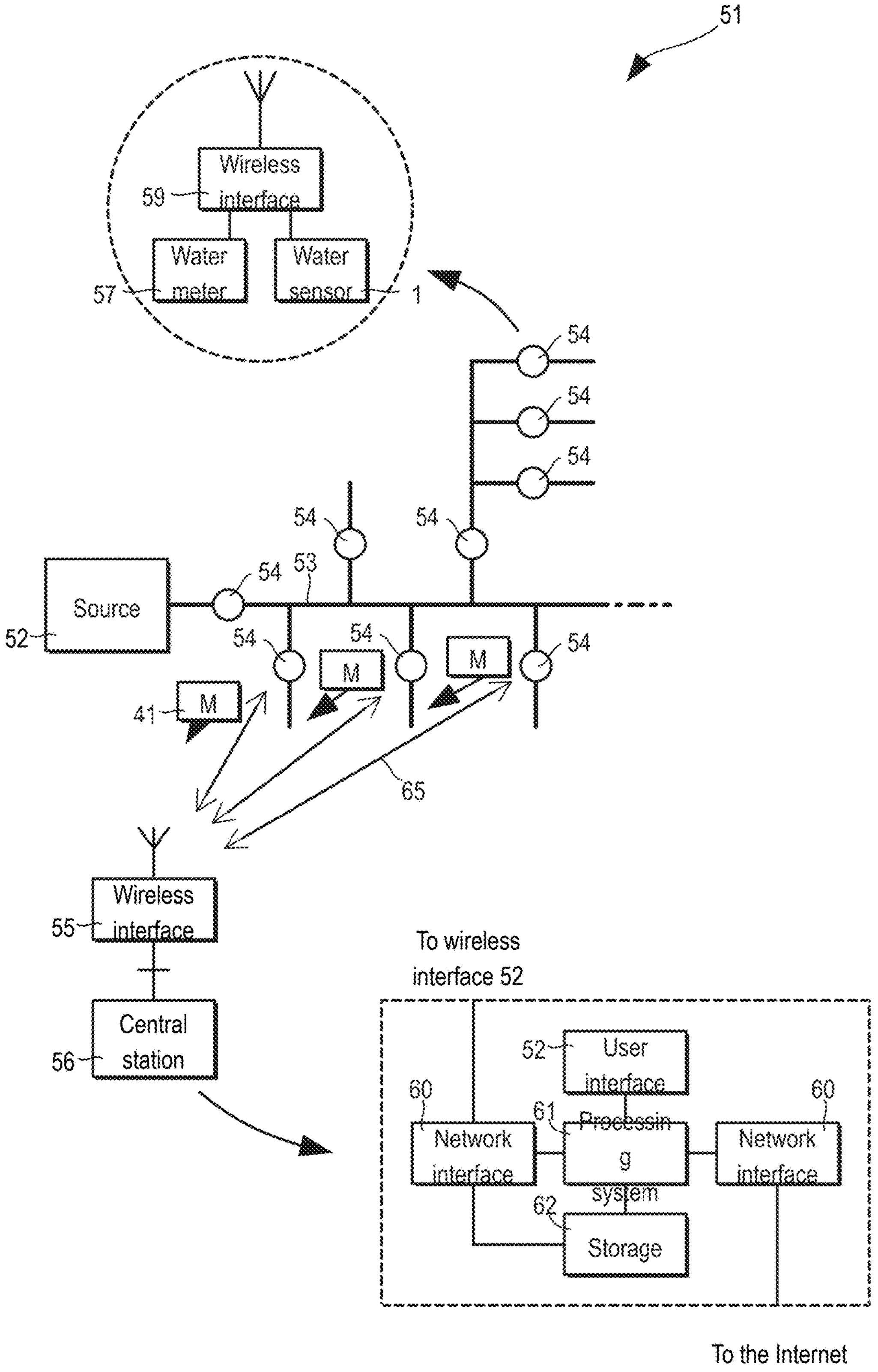
FIG. 8 is a schematic diagram of a water delivery network.

The apparatus 1 also includes a network interface 24 preferably in the form of a wireless communications network interface. The wireless communications network is preferably a low-power, wide-area (LPWA) network, such as LoRa®, which may communicate directly with a central node 56 (FIG. 8).

Figure 3:
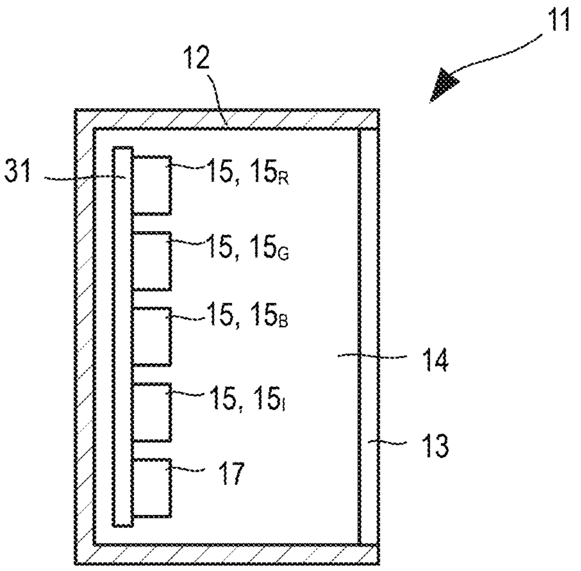
FIG. 3 is a schematic side view of an example of a sensor unit.

Referring to FIG. 3, the optical sensor 11 may comprise a printed circuit board (PCB) 31 supporting the at least one light source 15 and at least one photodetector 17. The at least one light source 15 and at least one photodetector 17 may be housed in the same enclosure 12. Each light source 15 can take the form of a light-emitting diode (LED). An integrated circuit (not shown) may provide one, two, three, four or more light sources 15 and the light detector 17. The one of more light sources include first, second, third and fourth light sources 15 (that is, first, second, third and fourth LEDs) each light source providing light at a different wavelength. For example, there may be infrared, red, green, and blue light sources $\mathbf{15}_I$, $\mathbf{15}_R$, $\mathbf{15}_G$, $\mathbf{15}_B$. respectively. The blue light source $\mathbf{15}_B$ may be omitted. In some cases, the light sources may emit, for example, white light, and a set of color filters (not shown) may be used to obtain light at different wavelengths. An optically-clear potting compound 14 may encapsulate the source(s) 15 and photodetector 17 and the optical window 13 may be omitted.

The measurement section 3 is configured such that the optical axis 21 (FIG. 4) of the sensor 11 is arranged perpendicular to the direction of the fluid flow 2 in the measurement section, thereby illuminating the cross section of the flow. The processing unit 22 and optical components 15, 17 can be housed in the same enclosure 12.

Figure 4:
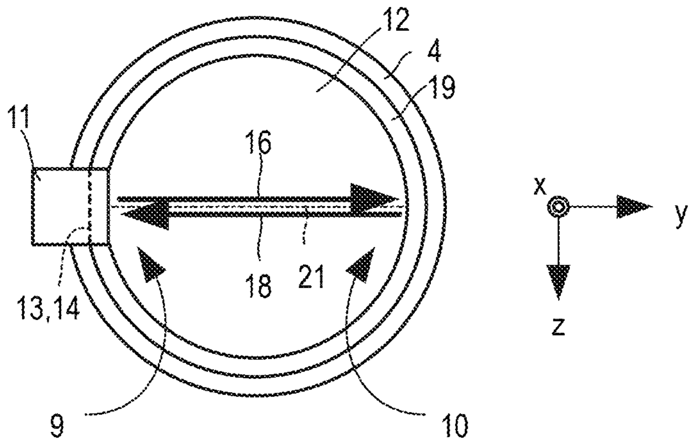
FIG. 4 is a schematic end view of an assembly of a sensor unit and a pipe.
Figure 5:
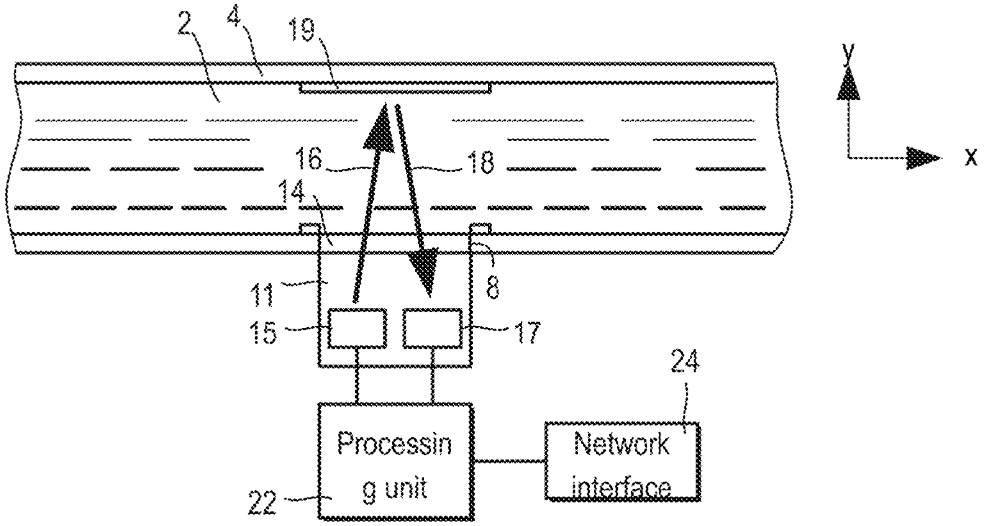
FIG. 5 is a schematic side view of an assembly of the sensor unit and a pipe shown in FIG. 4 and a processing unit.

Referring also to FIGS. 2 and 4, the sensor 11 may be inserted into the port 8 in the measurement section 3.

Light 16 is sent through the optical window 13 and/or potting compound 14 into the inside 6 of the flow tube 4. A white diffuse reflector 19, for example, in the form of an annulus of suitable material, is disposed inside the pipe 4 to increase the signal-to-noise ratio.

Preferably, the at least one optical source 15 is orientated with respect to diffuse reflector 19 the so that light 16 is directed normally (that is, 90 degrees) at the diffuse reflector 19 so that it reflected back on itself, back along optical axis 21. In other words, the light 16 is not directed at an oblique angle (for instance, 45 degrees) at the diffuse reflector 19.

Figure 6:
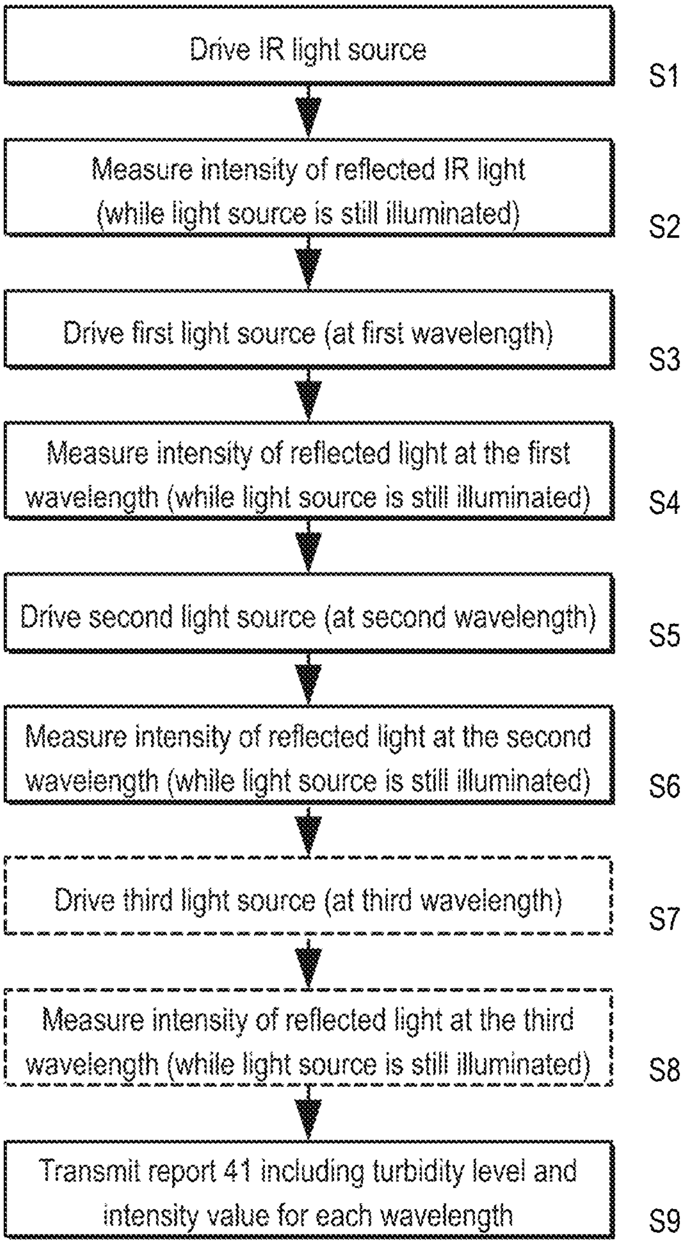
FIG. 6 is a process flow diagram of a method of operating the sensor unit.

Referring to FIG. 6, the photodiode 17 measures the intensity of infrared light 18 reflected by particles from the infrared LED (step S1 and S2). This is used to measure turbidity. The photodiode 17 measures the light 18 reflected by the diffuse reflector from each of the LEDs 15 in sequence, one at a time (steps S3 to S8). In other words, a first light source 17 is activated for a given time (step S3) and, while it is active, the photodiode 17 measures the intensity of the reflected light (step S4). The first light source 15 is deactivated and then the next light source 15 is activated for a given time (step S5) and, while it is active, the photodiode 17 measures the intensity of the reflected light (step S6) and so on. The given time and a repetition rate (in other words, how often a measurement is taken) may depend on flow rate. The signal decreases if particles (not shown) in the water 2 absorb light at a specific color (i.e., a specific wavelength). The sensor 11 collects the values at different colors and computes a turbidity level and respective raw intensity level of each color of light, e.g., intensity levels for red, green and, optionally, blue light. Other colors can be used, for example, yellow, depending on the color space of interest. After correcting each value for the turbidity level, the sensor transmits a report 41 (or "message") of the four values, namely turbidity and RGB triplets or RG pairs (if only R and G channels are present) (step S9). The message 41 can include other information such as a code or alarm level.

By using a simple optical sensor (i.e., one in which the optical sources and detectors can be mounted in the same board and/or provided by a single IC), lower-cost, high-volume electronic circuits can be used. By using a backscattering geometry arranged perpendicular to the water flow, a simpler design can be used which reduces complexity of installation. By performing measurement in-line, there is no need for additional components for flow diversion and conditioning and waste management.

Referring in particular to FIG. 1, the use of the diffuse reflector 19 can allow the optical components to be positioned on one side 9 of the measurement section 3 thereby reducing mechanical and manufacturing complexity. Additionally, the reflector 19 can be suitably shaped to facilitate its integration into arbitrarily shaped measurement sections.

Figures 7A, 7B, 7C:
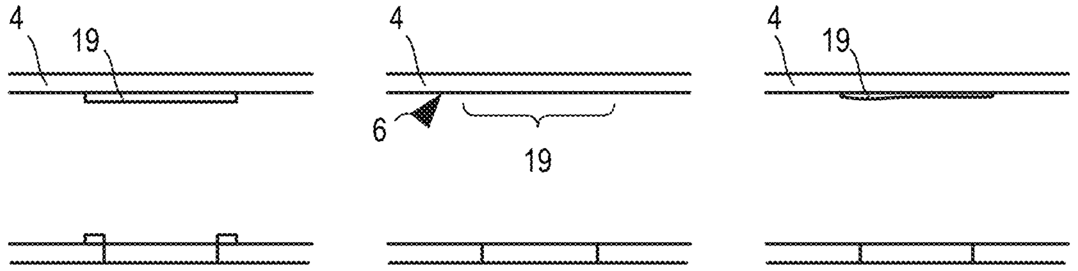
FIGS. 7A, 7B and 7C are side views of three reflectors for use in the measuring apparatus.

Referring to FIG. 7A, the diffuse reflector 19 can take the form of annulus or part of an annulus $\mathbf{19}_{arc}$ (or "arced cylindrical section") formed of suitable material, such as polycarbonate, PTFE or ODM98.

Referring to FIG. 7B, the inside surface 7 of the pipe 4 itself may provide the diffuse reflector 19, especially if the pipe is formed from a suitable plastic material. In some cases, the surface 7 may be prepared, e.g., roughened, to provide sufficient diffusiveness.

Referring to FIG. 7C, the diffusive reflector 19 may take the form of a coating of suitable material applied to inside surface 7 of the pipe 4. Suitable materials for the diffuse reflector include titanium dioxide nanoparticles, nanocellulose-based materials, PTFE-based materials and ODM98.

The sensor 1 uses low-cost, low-power consumer electronic components, such as those found in wearable electronic devices (e.g., smart watches) which allow the system to be battery powered with long lifetime.

Referring to FIG. 8, a drinking water distribution network 51 is shown which includes a source 52 of drinking water, a network of pipes 53, water measurement nodes 54, a wireless access point 55 and a central station 56.

Each water measurement node 54 includes a fiscal water meter 57, a water sensor 1 and a wireless network interface 59.

The central station 56 includes a first network interface 60 for interfacing with the water measurement nodes 54, a processing system 61, storage 62, a user interface 52 and an optional second network interface 60, e.g., for interfacing with the Internet, as shown.

The sensor 1 can communicate information back to a processing unit or gateway unit (not shown) which reports the information back to a centralized station 56 via wireless links 65 which can then remotely monitor the quality of the water.

The sensor 1 may be mounted inside or next to a smart water meter 57 and is directly connected to the meter electronics, which manages the measurement schedule and is responsible for reporting the measurement value to a centralized system 56.

The lower power consumption, lower cost and the possibility to install the sensor next to an existing or co-installed water meter while sampling the main water stream help to enable a large number of sensors to be deployed at the point of use in a drinking water distribution network 51 thereby providing valuable real-time data on the characteristics of the water being delivered to the end user.

The information allows for a faster response to issues which might cause customer complaints and cause issues with the quality of the delivered water and a better monitoring of network operation which can enable a more flexible operation of the network.

The information collected by the centralized system can be correlated with the geographical position of the water meter node 54 and the known topology of the network so that in case of an event which leads to changes in one of the measured properties the system can estimate the most probable location of the origin of the detected change.

Figure 9:
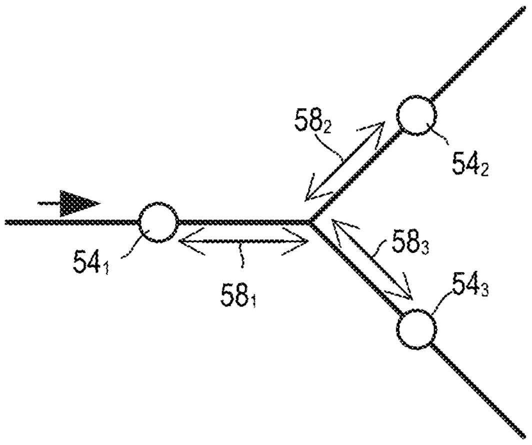
FIG. 9 is a schematic diagram of a part of a water delivery network.

Referring to FIG. 9, a simple example of a pipe network is shown in which water flows through a first water measurement node $\mathbf{54}_1$ into a first pipe section $\mathbf{58}_1$ which splits into second and third pipe sections $\mathbf{58}_2$, $\mathbf{58}_3$ each having a respective node $\mathbf{54}_2$, $\mathbf{54}_3$. If the first and second water measurement nodes $\mathbf{54}_1$, $\mathbf{54}_2$ measure low values of turbidity but the third water measurement node $\mathbf{54}_3$ measures a high value of turbidity, then the probable location is in the third pipe section $\mathbf{58}_3$.

The central station 56 can use a model (not shown) to simulate ingress of contaminant. The results can be displayed via the user interface.

The most probable location of the origin of the detected change can be found, for example, by identifying the population of meters which measure a change or drift in the measured property and tracking the section of the network that feeds water to the meter population. Additionally, meters can be clustered based on the magnitude and time evolution of the measured change, to provide an estimate of the pipe section where the issue might be arising to mitigate the effect of false positive readings from single sensors.

The centralized system can also provide an estimate of the severity of the issue affecting the network by correlating the number of meters which detect the change in the measured property with the magnitude of the measured change. This may be used to determine whether urgent action is required.

For example, a slow drift of the measured parameter(s) can indicate a minor issue in the network, so a low priority alarm can be raised, linked to a time estimate for when the parameters will be out of tolerance and maintenance will be required. This can further be connected to the number of meters (hence the portion of the network) being affected by the issue. This way, smaller issues which however affect a large household population could still be considered as a severe issue and dealt with high priority.

Furthermore, the centralized system can also infer the characteristics of the cause of the measured change by correlating the degree of discoloration with the color of the dissolved material and/or the change in ORP, and/or the change in turbidity, for example distinguishing the ingress of soil through a damage pipe, such as clay or red sand, versus the presence of rust due to pipe corrosion. The information can be fed to the maintenance crews in order to provide them with more accurate instruction on the maintenance operation required, reducing the number of site visits.

As an example, a discoloration value indicating the presence of red/brown dissolved matter can be correlated with the change in ORP. The presence of rust has been shown to induce a relatively small change in ORP potential, while the ingress of soil will quickly exhaust the chlorine disinfectant in the water supply causing a sharp decrease in ORP potential. So based on the change in ORP potential it is possible to discriminate between ingress of soil particles in a broken pipe against the presence of iron oxide due to corrosion in the pipe. The information can then be used to direct the maintenance effort based on the advanced knowledge on the type of issue being experienced in the network.

As an additional example, when an increase in turbidity is observed in a section of the network, this can be monitored against the measured ORP value. Suspended particles should not change ORP significantly, however they sustain bacterial growth. Bacterial proliferation will use up the disinfectant in the water supply, so that the issue can be considered a low or high priority based on the observed changed in ORP: low priority if no change in ORP is observed, high priority if a reduction in ORP potential is observed.

It will be appreciated that many modifications may be made to the embodiments hereinbefore described.

The invention claimed is:

1. An apparatus for measuring at least one optical property of a fluid, the apparatus comprising:

a measurement section comprising:

a conduit for a fluid;

at least one light source;

at least one photodetector;

a diffuse reflecting surface; and a processing unit for processing at least one signal received from the at least one photodetector for use in determining at least one optical property of a fluid, wherein the at least one optical property includes color of the fluid, turbidity of the fluid, or both the color of the fluid and the turbidity of the fluid, wherein the at least one light source, the at least one photodetector and the diffuse reflecting surface are configured such that, when light is emitted by the at least one light source and the fluid is in the conduit, the light passes through the fluid and is reflected from the diffuse reflecting surface towards the at least one photodetector.

2. The apparatus of claim 1, wherein:

the light emitted by the at least one light source passes along an optical axis which is normal to the diffuse reflecting surface or which is within 10 degrees from the normal to the diffuse reflecting surface.

3. The apparatus of claim 1, wherein the at least one light source and the at least one photodetector are disposed on one side of the measurement section.

4. The apparatus of claim 1, wherein the conduit is a tube.

5. The apparatus of claim 1, wherein the diffuse reflecting surface is curved.

6. The apparatus of claim 5, wherein the diffuse reflecting surface is an arced section of a cylinder.

7. The apparatus of claim 1, wherein the diffuse reflecting surface is or is substantially white.

8. The apparatus of claim 1, wherein the diffuse reflecting surface comprises a coating on an inner surface of the conduit.

9. The apparatus of claim 1, wherein the at least one light source and the at least one photodetector are provided in a sensor unit comprising a housing.

10. The apparatus of claim 1, wherein the processing unit is configured to calculate a given parameter indicative of a quality of the fluid in dependence upon the at least one signal received from the at least one photodetector.

11. The apparatus of claim 1, wherein the fluid is a liquid.

12. The apparatus of claim 11, wherein the fluid is water.

13. A fluid meter comprising:

a unit housing, comprising:

an apparatus for measuring fluid flow through the meter; and the apparatus of claim 1.

14. A system comprising:

a fluid meter; and the apparatus of claim 1;

wherein the fluid meter and the apparatus are discrete units arranged such that fluid is communicated through the meter and then through the apparatus or vice versa.

15. An apparatus for measuring at least one optical property of a fluid, the apparatus comprising:

a measurement section comprising:

a conduit for a fluid;

at least one light source;

at least one photodetector;

a diffuse reflecting surface; and a processing unit for processing at least one signal received from the at least one photodetector for use in determining at least one optical property of a fluid;

wherein the at least one light source, the at least one photodetector and the diffuse reflecting surface are configured such that, when light is emitted by the at least one light source and the fluid is in the conduit, the light passes through the fluid and is reflected from the diffuse reflecting surface towards the at least one photodetector, wherein:

the light emitted by the at least one light source passes along an optical axis which is parallel to the normal to the diffuse reflecting surface or passes along an optical axis which is perpendicular to an axis of the conduit comprising a cylindrical conduit.

16. An apparatus for measuring at least one optical property of a fluid, the apparatus comprising:

a measurement section comprising:

a conduit for a fluid;

at least one light source;

at least one photodetector;

a diffuse reflecting surface; and a processing unit for processing at least one signal received from the at least one photodetector for use in determining at least one optical property of a fluid;

wherein the at least one light source, the at least one photodetector and the diffuse reflecting surface are configured such that, when light is emitted by the at least one light source and the fluid is in the conduit, the light passes through the fluid and is reflected from the diffuse reflecting surface towards the at least one photodetector, wherein:

the light emitted by the at least one light source passes along an optical axis which is perpendicular to a plane containing an axis of the conduit comprising a cylindrical conduit.

17. An apparatus for measuring at least one optical property of a fluid, the apparatus comprising:

a measurement section comprising:

a conduit for a fluid;

at least one light source;

at least one photodetector;

a diffuse reflecting surface; and a processing unit for processing at least one signal received from the at least one photodetector for use in determining at least one optical property of a fluid;

wherein the at least one light source, the at least one photodetector and the diffuse reflecting surface are configured such that, when light is emitted by the at least one light source and the fluid is in the conduit, the light passes through the fluid and is reflected from the diffuse reflecting surface towards the at least one photodetector, and wherein the at least one light source is or is substantially monochromatic and the at least one photodetector is broadband or vice versa.

18. An apparatus for measuring at least one optical property of a fluid, the apparatus comprising:

a measurement section comprising:

a conduit for a fluid;

at least one light source;

at least one photodetector;

a diffuse reflecting surface; and a processing unit for processing at least one signal received from the at least one photodetector for use in determining at least one optical property of a fluid;

wherein the at least one light source, the at least one photodetector and the diffuse reflecting surface are configured such that, when light is emitted by the at least one light source and the fluid is in the conduit, the light passes through the fluid and is reflected from the diffuse reflecting surface towards the at least one photodetector, and wherein at least one of the at least one light source, or at least one of the at least one photodetector, or both, are operable in an infrared band of an electromagnetic spectrum.

* * * * *